United States Patent [19]

Kane

[11] Patent Number: 4,691,708
[45] Date of Patent: Sep. 8, 1987

[54] OPTICAL PRESSURE SENSOR FOR MEASURING BLOOD PRESSURE

[75] Inventor: James Kane, Miami, Fla.

[73] Assignee: Cordis Corporation, Dade, Fla.

[21] Appl. No.: 838,125

[22] Filed: Mar. 10, 1986

[51] Int. Cl.⁴ .............................................. A61B 5/02
[52] U.S. Cl. .................................... 128/667; 128/675; 128/748; 73/705
[58] Field of Search .............................. 128/672–675, 128/748, 665–667, 633–634; 73/705, 708, 715

[56] References Cited

U.S. PATENT DOCUMENTS

| | | | |
|---|---|---|---|
| 3,215,135 | 11/1965 | Franke | 128/675 |
| 3,267,932 | 8/1966 | Valliere | 128/675 |
| 3,789,667 | 2/1974 | Porter et al. | 128/748 X |
| 4,210,029 | 7/1980 | Porter | 128/673 X |
| 4,487,206 | 12/1984 | Aagard | 128/673 X |
| 4,543,961 | 10/1985 | Brown | 128/748 X |
| 4,548,505 | 10/1985 | Ono | 128/634 X |
| 4,593,701 | 6/1986 | Kobayashi et al. | 128/673 X |
| 4,611,600 | 9/1986 | Cohen | 128/667 |

OTHER PUBLICATIONS

Matsumoto et al., "The Development of a Fibre Optic Catheter Tip Pressure Transducer", J. of Med. Engr. and Technology, vol. 2, No. 5.

Primary Examiner—Kyle L. Howell
Assistant Examiner—Angela D. Sykes
Attorney, Agent, or Firm—Tarolli, Sundheim & Covell

[57] ABSTRACT

The optical blood pressure catheter includes an elongated optical fiber located within the lumen of the catheter for transmitting light received at its proximal end to its distal end where the light is reflected from a mirror and the reflected light is received at the distal end and transmitted back to the proximal end thereof. A pressure transducer is located at the distal end of the catheter and includes a mirror which is spaced forwardly of the distal end of the optical fiber and is fixed in position relative thereto so as to receive and reflect light emitted from the distal end of the optical fiber and back into the distal end thereof. A side port is provided in the catheter housing adjacent its distal end and the side port is sealed with a pressure-responsive membrane responsive to pressure acting transversely thereof. The pressure-responsive memberane is coupled to the distal end of the optical fiber so that the distal end of the optical fiber is displaced in dependence upon pressure acting upon the membrane. The catheter is vented to atmospheric pressure permitting pressure readings greater or less than that of atmospheric pressure.

7 Claims, 7 Drawing Figures

OPTICAL PRESSURE SENSOR FOR MEASURING BLOOD PRESSURE

BACKGROUND OF THE INVENTION

This invention relates to the art of measuring intravascular blood pressure and, more particularly, to apparatus for directly measuring blood pressure at the location of interest by means of a catheter having a transducer tip insertable into the blood stream.

Catheters have been used in the art for monitoring variations in pressure within the blood stream at various locations throughout the cardiovascular system. It has been accepted practice to insert the distal end of a catheter into a blood vessel and then connect the proximal end of the catheter outside the body to an external transducer at which pressure variations are measured. Such external transducers are considered relatively inexpensive and employ disposable fluid filled catheters. However, in use such catheters require periodic flushing to avoid thrombus formation. Also, the frequency response characteristics are often compromised by the mechanical properties of the catheter, inclusion of small air bubbles and by body motion artifact. The blood pressure must be transmitted from the interior of the blood vessel through the catheter tubing by means of the fluid column therein before it can act on the external transducer. Consequently, the frequency response for such an external transducer is also compromised by the relatively large mass of the fluid column within the catheter tubing.

Other approaches to measuring intravascular blood pressure have included employing catheter tip transducers insertable into the blood stream. Such catheter tip transducers provide direct pressure monitoring in that they transduce blood pressure at the region of interest rather than attempting to couple the dynamic waveform hydraulically, as in the external transducers. Many of the catheter tip transducers employ semiconductors and other sensing elements of the resistive and/or capacitive variety at the catheter tip. An electrical signal is generated or modulated at the transducer and transmitted through the length of the catheter to meters and the like located externally of the body being tested. Such semiconductor tip transducers are expensive and, hence, the high cost is not compatible with their being disposable units. Instead, there is a tendency to reuse the product and, despite sterilizing or autoclaving, there remains a potential to transfer proteins, which may be antigenic, from one patient to a successive one. Another potentially troublesome feature of such semiconductor transducer tips is the use of electricity to power the sensor. The use of electricity not only renders the device susceptible to electromagnetic interference, but also introduces the possible hazard of arrhythmia induction.

To overcome some of the noted difficulties, other attempts in determining blood pressure in a cardiovascular system have included catheters employing optically based pressure transducer tips at the distal end. Such devices typically take the form as illustrated in U.S. Pat. No. 3,249,105 to Polyanyi, and Franke U.S. Pat. No. 3,215,135. Each of these devices employs a catheter having fiber optic means extending the length of the catheter to the distal end thereof at which the fiber optic means is in optical communication with a pressure transducer. The pressure transducers in Polyanyi and Faranke, supra, take the form of a diaphragm covering the end hole of the catheter. The diaphragm is located in front or distal to the end of the fiber optical means and then receives light and reflects it back into the fiber optic means for transmission to an externally located meter. Since the transducer tip is inserted into the blood stream of a patient, the blood pressure deflects the diaphragm causing modulation of the light intensity so that the meter provides an indication of blood pressure. Such catheters employing diaphragm covered end holes actually measure total pressure rather than the desired measurand; namely, static pressure. Thus, by aligning the end hole of a catheter with the direction of blood flow, kinetic energy terms are introduced. If the catheter end hole is directed upstream, the kinetic term will be added to the pressure, and, if the end hole is facing downstream, the kinetic term will be subtracted from the pressure. The magnitude of the error will vary with flow rate. This error will vary during the course of a cardiac cycle and will distort the shape and magnitude of a pressure wave. In the pulmonary artery, the kinetic pressure may be on the order of 10% of total pressure at rest and 50% of total pressure at a cardiac output equal to three times that at rest. The importance of the kinetic pressure error is particularly great in stenotic areas where velocities are high.

The noted problems with catheters employing diaphragm covered end holes to monitor pressure may be alleviated with a tip transducer that employes side port monitoring of pressure rather than end hole monitoring of pressure. The kinetic contribution is minimal when measuring pressure perpendicular to the blood flow. One such device is known and is reported in a 1978 article entitled "The Development of Fiber Optic Catheter Tip Pressure Transducer", Journal of Medical Engineering and Technology, Vol. 2, No. 5, by H. Matsumoto and M. Saegusa. As disclosed in that article, the Matsumoto optical sensor employs a tipped transducer having side port monitoring of pressure. The pressure transducer measures pressure acting at right angles to blood flow. A membrane is responsive to the pressure and causes movement of a mirror, which is mounted in cantilevered fashion to the membrane, within the cavity of the transducer tip. The mirror serves to reflect light received from fiber optic means extending the length of the catheter so that the intensity of light returned by way of the fiber optic means to a measuring device located outside the body is modulated in accordance with the static pressure. However, this structure requires precise alignment between the distal end of the fiber optic and the cantilevered mounted mirror so that the deflected light as measured by the externally located meter will be properly indicative of the static pressure. Additionally, there is a nonlinearity in the response characteristics of such a device both because the cantilevered mounted mirror undergoes an angular displacement and nonlinear displacement.

SUMMARY OF THE INVENTION

It is an object of the present invention to provide a catheter having an optical fiber pressure transducer tip constructed in a manner so that it is sufficiently inexpensive to be disposable.

It is a still further object of the present invention to provide an improved optical fiber pressure transducer employing side port measuring of static pressure as opposed to end hole structure which is subject to kinetic pressure errors.

It is a still further object of the present invention to provide an improved construction wherein a membrane covered side port is responsive to pressure to displace the distal end of an optical fiber within the catheter to change the amount of light reflected back from a fixed mirror mounted forwardly thereof for thereby modulating the intensity of the light reflected back into the optical fiber in proportion to the pressure forces acting transversely of the membrane covered side port.

It is a still further object of the present invention to provide an improved construction wherein pressures greater or less than atmospheric pressure may be measured with an optical pressure sensor.

In accordance with the present invention, the optical blood pressure sensor includes an elongated tubular catheter having a proximal end and a distal end with the latter adapted to be inserted into a passageway within a cardiovascular system or the like. An elongated light transmitter, such as an optical fiber, is carried within the catheter and extends essentially throughout the length thereof for purposes of receiving light at the proximal end of the catheter and transmitting it to the distal end thereof where it is reflected from a fixed mirror located at the end of the catheter and returned to the light transmitter for passage back to the proximal end. At least a portion of the length of the optical fiber spaced from the distal end thereof is secured to the inner walls of the catheter so that the distal end of the optical fiber is cantilevered inwardly of the walls of the catheter at an angle relative to the fixed mirror. A side port is provided in the catheter adjacent the distal portion of the optical fiber and a pressure sensitive membrane covers the opening. Biasing means couples the membrane with the distal end of the optical fiber so that the distal end is displaced as the membrane responds to pressure acting transversely of the catheter so as to attenuate the amount of light reflected from the mirror back into the distal end of the optical fiber in dependence upon the pressure exerted on the membrane.

In accordance with a still further aspect of the present invention, the catheter is vented to the atmosphere and the membrane responds to pressures above or below that of atmospheric pressure and the light reflected back into the optical fiber varies with such pressures above and below that of atmospheric pressure.

BRIEF DESCRIPTION OF THE DRAWINGS

The foregoing and other objects and advantages of the present invention will become more readily apparent from a consideration of the following description as taken in conjunction with the accompanying drawings, wherein.

DETAILED DESCRIPTION OF THE PREFERRED EMBODIMENT

Figure 1:
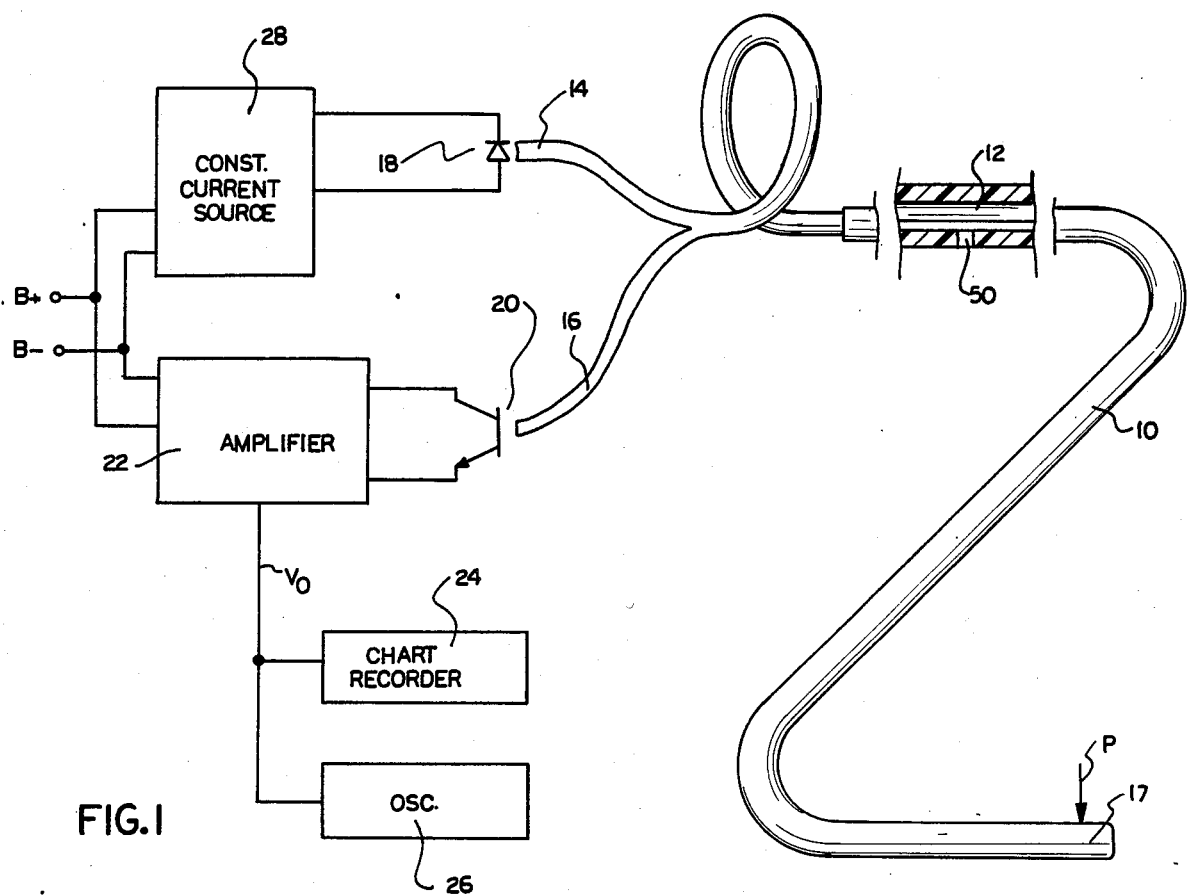
FIG. 1 is a schematic illustration of the catheter in conjunction with one application of this invention.

Reference is now made to the drawings wherein the showings are for purposes of illustrating a preferred embodiment only, and not for limiting the same. FIG. 1 illustrates an application of the invention as applied to measurement of pressure within a patient's cardiovascular system and includes an elongated single lumen catheter 10 containing an optical fiber 12 which extends essentially throughout the length of the catheter. The optical fiber 12 is bifurcated at its proximal end defining two legs 14 and 16. Leg 14 is positioned to receive light from an ultra bright light emitting diode (LED) 17 for transmission through the length of the fiber 12 to its distal end at which there is located a pressure transducer 18. The transducer 18, to be described in greater detail hereinafter, is responsive to pressure forces acting transversely of the catheter and these forces are represented by the arrow P in FIG. 1. As will be brought out in greater detail, light transmitted by way of the optical fiber through the transducer 18 is modulated in its intensity inversely proportional to the pressure P and the intensity modulated light travels back through the optical fiber 12 and then through leg 16 and is sensed by a photodiode 20.

The photodiode 20 is connected with suitable circuitry, including an amplifier 22, for providing an output voltage $V_O$ having a magnituide which varies in dependence upon the amount of current flowing through the photodiode and which, in turn, varies with the amount of light it receives from the optical fiber leg 16. The output voltage $V_O$ from the amplifier may then be supplied to a suitable readout, such as a chart recorder 24 and an oscilloscope 26. Other outputs including digital voltmeters and the like may be employed as desired.

The light emitting diode 17 will be supplied with constant current from a constant current source 28, such as on the order of 30 milliamps with the diode having a power dissipation of approximately 60 milliwatts. The photodiode 20 may take the form of silicon PIN (positive intrinsic negative) photodiode. The sensitivity of the photodiode 20 may be on the order of 20 amperes per watt. The amplifier may conveniently have a gain adjustment for varying the magnitude of the output voltage $V_O$. Additionally, an offset adjustment may be provided for an initial zeroing operation.

As shown in FIG. 1, the optical fiber 12 is looped at least once prior to insertion into the proximal end of catheter 10. This is done to enhance light distribution throughout the fiber. The catheter 10 may suitably take the form of a single lumen, thin walled catheter, such as that provided by Cordis Corporation, and known as Cordis FR5 thin walled catheter. This catheter may have a diameter on the order of 0.066 inches and is constructed of plastic material, such as polyurethane. The optical fiber 12 may take various forms well known in the art and, for example, may take the form of a silica core having a core diameter on the order of 368 micrometers. The core is covered with a cladding which may also be of silica and with a clad diameter on the order of 400 micrometers, nominally. Other optical fibers may be used, such as one having a polymethylmethacrylate core and a fluorcarbon cladding. Also, the optical fiber used may not be confined to one with a core cladding construction, but may be a step index fiber or a graded index fiber.

Attention is now more specifically directed to FIGS. 2–5 which illustrate the invention in greater detail. Adjacent the distal end of the catheter 10, there is provided an opening or side port 30. This side port is sealed with a membrane 32. The membrane 32 exhibits elastomeric properties and may be constructed of silastic or polyurethane or other suitable material having elastomeric properties. The membrane is secured to the side port 30 in the catheter as by fusing or other suitable bonding. Additionally, the membrane is preferably optically opaque. One material for this is a black pigmented plastic. Pressure applied transversely of the membrane will cause it to deflect inwardly or outwardly depending on the direction of pressure with the deflection being on the order of 0.001 inches for every 100 mm-Hg applied.

The distal end of the catheter is closed as with a block 40 of plastic material, such as polyurethane or urethane which is fused or otherwise suitably bonded to the distal end of the catheter 12. The interior surface of block 40 is coated with a suitable reflective material to define a mirror 42. This mirror may be alternatively of polished metal or metal coated plastic.

Figure 3:
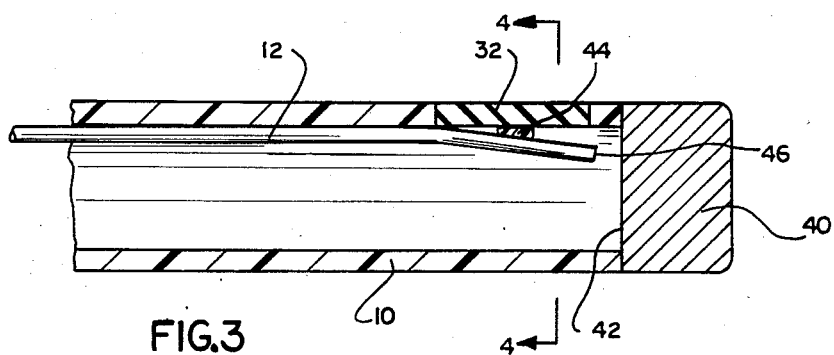
FIG. 3 is an enlarged longitudinal sectional view of the distal end of the optical pressure sensor taken along line 3—3 looking in the direction of the arrows in FIG. 2.

The optical fiber 12 extends within the lumen of the catheter 10 throughout essentially the entire extent of the catheter, but terminates short of the distal end at which the mirror 42 is located. For a portion of its length, the optical fiber is fused to the more rigid inner wall of the catheter 10. The fusing stops short of membrane 32 so that the optical fiber is supported in cantilever fashion and cants inwardly as is shown in FIG. 3. This is assisted by a wedge-shaped bias support 44 which interconnects the distal end of the optical fiber with a portion of the membrane 32. This bias support may be constructed of silastic or polyurethane material.

Figure 4:
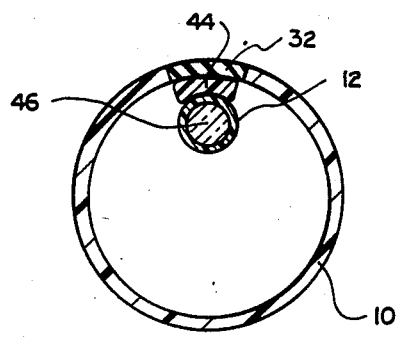
FIG. 4 is an enlarged cross sectional view at the distal end of the optical pressure sensor taken along line 4—4 looking in the direction of the arrows in FIG. 3.

The distal end 46 of the optical fiber is preferably polished, forming a somewhat flat face as is shown in FIGS. 3 and 4. Consequently, a cone of light is emitted from the polished end 46 of the optical fiber which is reflected from the mirror 42. Some of the reflected light returns through the optical fiber for transmision to the proximal end thereof. The bias support 44 maintains the distal end of the optical fiber canted inwardly so that the optical axis of the fiber makes an angle greater than 90° with the surface of mirror 42. The lumen of the catheter is vented to the atmosphere by means of an aperture 50 located at the proximal end of the catheter at the point where the catheter is not inserted into the human body. This construction, then, permits venting of pressure which is greater or less than atmospheric pressure. As the pressure increases beyond atmospheric pressure, the membrane will bow inwardly causing the cantilevered distal tip of the optical fiber to bend inwardly even more, increasing the angle with the mirror 42 whereby less light is reflected back into the optical fiber. Conversely, as the pressure decreases, and even becomes less than atmospheric pressure, the angle will decrease towards 90° and more light will be reflected back into the optical fiber from the mirror 42. This operation may be better understood with reference to FIGS. 5A through 5C.

Figures 5A, 5B, 5C:
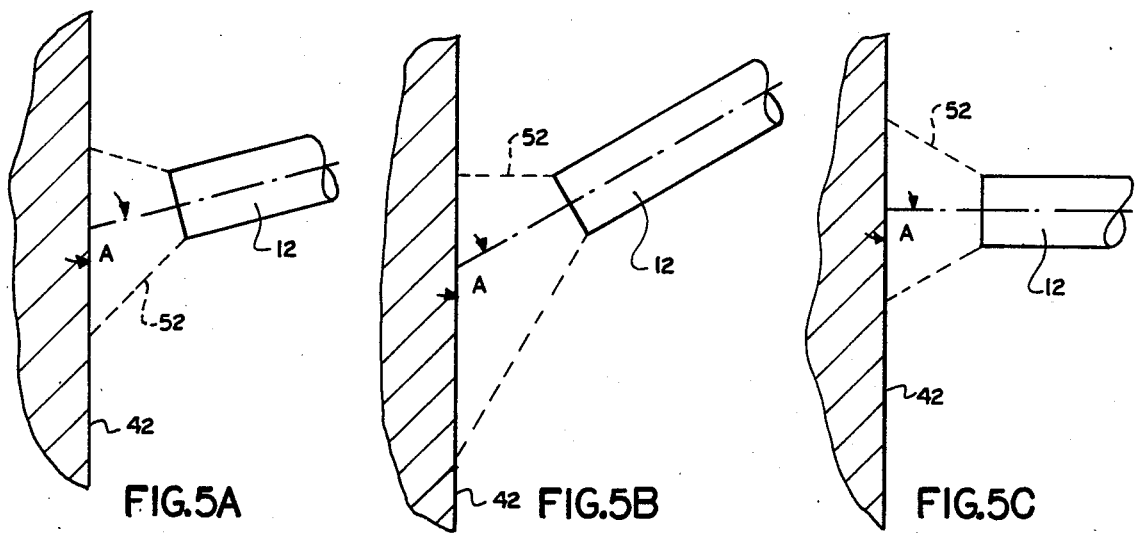
FIG. 5A is an enlarged schematic illustration showing one position of the optical fiber relative to the fixed mirror.
FIG. 5B is a view similar to that of FIG. 5A showing a second position of the optical fiber relative to the fixed mirror.
FIG. 5C is another illustration similar to FIG. 5A showing still a further position of the optical fiber relative to the fixed mirror.
Figure 2:
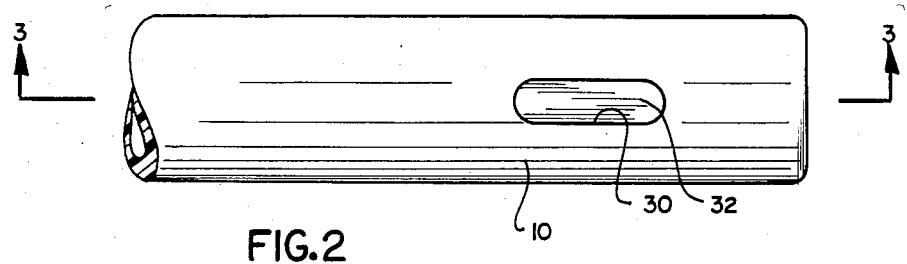
FIG. 2 is an enlarged view of the distal end of the optical pressure sensor.

With reference now to FIG. 5A, this represents the normal relationship between the cantilevered distal tip of the catheter 12 and the mirror 42. The included angle A between the surface of mirror 42 and the optical axis OA of the optical fiber 12 represents an angle greater than 90°. This, as discussed hereinbefore, is achieved by biasing the cantilevered distal tip of the optical fiber by means of the bias support 44. As light exits from the optical fiber toward the mirror, there is defined a light cone 52. As the included angle A increases, the light within the light cone 52 that is reflected back into the optical fiber will decrease. This is seen, for example, with reference to FIG. 5B in which the included angle A has substantially increased because of an increased level of pressure acting transversely on the membrane 32. It is apparent that substantially less light will be reflected back into the optical fiber at this pressure level than that which takes place at the pressure level represented by FIG. 5A. When the atmospheric pressure is greater than that of blood pressure exerted on the membrane 32, then, the cantilevered distal tip of the optical fiber 12 will bend outwardly against the resilient bias support 44 so that the included angle A approaches 90°, causing an increase in the amount of light reflected from the mirror back into the optical fiber. Consequently, then, the intensity of light returning at the proximal end of the catheter at the fiber leg 16 will vary inversely with the pressure forces P applied to the membrane 32. This is sensed by the photodiode 20 and amplified by amplifier 22 to provide the operator with a readout, as with the chart recorder 24 or the oscilloscope 26.

It is suggested that the instrumentation be zeroed or calibrated prior to insertion of the catheter into a patient. Thus, the amplifier 22 may be adjusted for gain so as to vary the magnitude of the output voltage $V_O$ with respect to a particular pressure reading. Also, the amplifier may be zeroed, as with a potentiometer, to zero out the effects of any back reflection or the like. This adjustment, then, may apply an offsetting bias so that the output voltage $V_O$ is equal to zero when the applied pressure P is equal to atmospheric pressure.

With the preliminary adjustments being made, the operator may now insert the distal end of the catheter 10 into a blood vessel, such as the pulmonary artery, of the patient, until the transducer tip reaches the site of interest. The aperture 50 at the proximal end of the catheter should be external of the patient's body so that atmospheric pressure is communicated through the lumen of the catheter to the distal end thereof. Pressure, greater than atmospheric, exerted in the direction P (see FIG. 1), will cause deflection of the membrane 32 in an inwardly direction causing less light to be reflected back into the optical fiber from the mirror 42. Conversely, pressure less than atmospheric will result in the distal tip of the optical fiber moving upwardly to increase the angle A toward 90°. With the distal end in place and power turned on, light emitted from diode 17 will be transmitted by way of the optical fiber leg 14 and then through the core of the optical fiber through the distal end of the catheter where the intensity of light will be modulated in dependence upon pressure acting on the membrane 32.

Although the invention has been described in conjunction with a preferred embodiment, it is to be appreciated that various modifications may be made without departing from the spirit and scope of the invention as defined by the appended claims.

Having described a specific preferred embodiment of the invention, the following is claimed:

1. Apparatus for measuring blood pressure in a cardiovascular system and comprising:

an elongated tubular catheter having a lumen and having a proximal end and a distal end with the latter being adapted to be inserted into a passageway within a cardiovascular system;

an elongated optical fiber having a proximal end and a distal end and carried within the lumen of said catheter and extending throughout substantially the entire length thereof for receiving light at the proximal end of said catheter and transmitting it to the distal end thereof;

light reflecting means located at the distal end of said catheter and having a flat light reflecting surface fixed in position forwardly of the distal end of said optical fiber for receiving light from the distal end of said optical fiber and reflecting at least a portion of the light back to the optical fiber for receiving light from the distal end of said optical fiber and reflecting at least a portion of the light back to the optical fiber for transmission to the proximal end of said catheter;

means for modulating the intensity of light reflected back to the proximal end of said catheter as a function of pressure forces acting transversely of the distal end of the catheter and including pressure transducer means carried by the catheter and located adjacent the distal end thereof, said catheter having an opening to one side thereof at a location adjacent the distal end thereof, membrane means covering said opening and being responsive to said pressure forces to deflect inwardly and outwardly of the catheter in dependence thereon, biasing means interposed between said membrane means and the distal end of said optical fiber for biasing the distal end of the optical fiber inwardly of said catheter so that the optical axis at the distal end of said fiber normally makes a greater than 90° angle with said flat light reflecting surface of said light reflecting means with said angle increasing with increased pressure forces and decreasing with reduced pressure forces to thereby modulate the intensity of light reflected from said reflecting means into the distal end of said optical fiber for transmission to the proximal end thereof.

2. Apparatus as set forth in claim 1 wherein said catheter has inner walls and said optical fiber is secured for a portion of its length to the inner walls of said catheter at a location spaced proximal of said membrane means so that the distal end of said optical fiber cants inwardly of said catheter.

3. Apparatus as set forth in claim 2, wherein the distal end of said optical fiber is essentially flat and is perpendicular to its optical axis.

4. Apparatus as set forth in claim 1 wherein said catheter includes means located adjacent its proximal end for venting the interior of the catheter to atmospheric pressure so that said means is responsive to pressure forces above and below atmospheric pressure.

5. Apparatus as set forth in claim 4 wherein said biasing means is constructed of material exhibiting elastomeric properties.

6. Apparatus as set forth in claim 5 wherein said biasing means is constructed of silastic material.

7. Apparatus as set forth in claim 5 wherein said biasing means is constructed of polyurethane material.

* * * * *